(12) United States Patent
Skladnev et al.

(10) Patent No.: US 6,487,439 B1
(45) Date of Patent: Nov. 26, 2002

(54) GLOVE-MOUNTED HYBRID PROBE FOR TISSUE TYPE RECOGNITION

(76) Inventors: Victor N. Skladnev, Vaucluse, NSW 2030 (AU); Richard L. Thompson, Killarney Heights, NSW 2087 (AU); Irwin Wunderman, 605 Eunice Ave., Mtn View, CA (US) 94040; David J. Bull, 21 Eastcore Rd N+Z, Epping, NSW 2121 (AU)

( * ) Notice: Subject to any disclaimer, the term of this patent is extended or adjusted under 35 U.S.C. 154(b) by 0 days.

(21) Appl. No.: 08/818,915

(22) Filed: Mar. 17, 1997

(51) Int. Cl.⁷ .................................................. A61B 5/00
(52) U.S. Cl. ........................... 600/476; 600/310; 356/41
(58) Field of Search ................................. 128/665, 664, 128/633, 634, 898; 600/473, 476, 310, 342, 341; 356/39, 41; 607/88, 92

(56) References Cited

U.S. PATENT DOCUMENTS

| | | | | |
|---|---|---|---|---|
| 3,647,299 A | | 3/1972 | Lavallee ........................ 356/41 |
| 3,910,701 A | | 10/1975 | Henderson et al. ............ 356/39 |
| 3,994,590 A | | 11/1976 | Di Martini et al. ......... 356/178 |
| 4,190,056 A | * | 2/1980 | Tapper et al. ................ 128/630 |
| 4,250,894 A | * | 2/1981 | Frei et al. .................... 128/774 |
| 4,545,386 A | * | 10/1985 | Hetz et al. |
| 4,580,569 A | * | 4/1986 | Petrofsky |
| 4,587,421 A | | 5/1986 | Robertson .................... 250/239 |
| 4,690,148 A | * | 9/1987 | Hess ........................... 128/639 |
| 4,856,527 A | * | 8/1989 | Karcher et al. ............. 128/634 |
| 4,869,260 A | * | 9/1989 | Young et al. .......... 182/662.04 |
| 4,942,877 A | | 7/1990 | Sakai et al. .................. 128/633 |
| 5,036,853 A | | 8/1991 | Jeffcoat et al. ............. 128/634 |
| 5,079,629 A | * | 1/1992 | Oz ................................ 358/100 |
| 5,090,410 A | * | 2/1992 | Saper et al. ................. 128/633 |
| 5,170,786 A | * | 12/1992 | Thomas et al. .............. 128/633 |
| 5,172,693 A | * | 12/1992 | Doody ........................ 128/633 |
| 5,337,744 A | * | 8/1994 | Branigan ..................... 128/633 |
| 5,348,002 A | * | 9/1994 | Caro ............................ 128/633 |
| 5,411,024 A | | 5/1995 | Thomas et al. .............. 128/634 |
| 5,413,099 A | * | 5/1995 | Schmidt et al. .............. 128/633 |
| 5,417,207 A | * | 5/1995 | Young et al. ................. 128/634 |
| 5,427,093 A | | 6/1995 | Ogawa et al. ............... 128/633 |
| 5,441,050 A | * | 8/1995 | Thurston et al. ............. 128/659 |
| 5,452,717 A | * | 9/1995 | Branigan et al. ............ 128/633 |
| 5,520,177 A | | 5/1996 | Ogawa et al. |
| 5,588,427 A | * | 12/1996 | Tien ............................ 128/633 |

OTHER PUBLICATIONS

Mendelson, Ph.D. et al., Design and Evaluation of a New Reflectance Pulse Oximeter Sensor, Medical Instrument, vol. 11, No. 4, pp. 187–173, 1988.

Neuman, M.R., In Medical Instrumentation: Application and Design, pp. 265–266, Webster, J.G. (ed) 2nd Ed. Boston: Houghton Miffliin, 1992.

* cited by examiner

*Primary Examiner*—Marvin M Lateef
*Assistant Examiner*—Shawna J Shaw
(74) *Attorney, Agent, or Firm*—Gottlieb, Rackman & Reisman, P.C.

(57) ABSTRACT

A probe configured as a finger tip of a glove used to recognize tissue types in a human patient and adapted to perform both optical and electrical measurements to diagnose tissue type while scanned over the surface of the tissue. Hybrid electronic technology reduces the size of the diagnostic elements. The necessary electrical connections are led down the finger and the glove to a remotely positioned control unit. The control unit provides power to the diagnostic device and analyzes the signals received from the device.

7 Claims, 2 Drawing Sheets

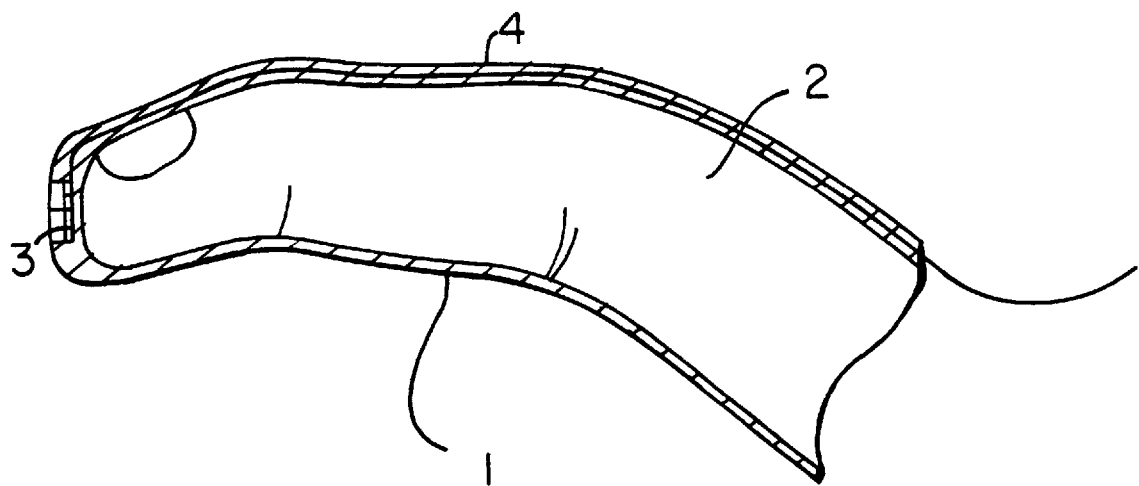
F I G. 1

GLOVE-MOUNTED HYBRID PROBE FOR TISSUE TYPE RECOGNITION

FIELD OF THE INVENTION

This invention relates to probes used to recognize tissue types in a human patient. The invention further relates to probes that perform both optical and electrical measurements to diagnose tissue type while scanned over the surface of the tissue.

BACKGROUND OF THE INVENTION

It is known to mount devices on the tips of the fingers of gloves for medical examination purposes. For example, it has been proposed to mount a small TV camera and light source on a glove to enable an area to be examined that is remotely sited in a patient. Such an apparatus would function in the manner of an endoscope. Provision has also been made for tissue samples to be taken from out-of-the-way places on the body using cutting devices on the tips of fingers.

SUMMARY OF THE INVENTION

The present invention makes possible tissue diagnoses at remote locations on a patient by the performance of combined electrical and optical tests. It is of particular value in locations such as the cervix which are readily accessed by hand. It also has application in surgical procedures where abnormal tissue such as burned or cancerous tissue must be removed. It is often important to remove all of the abnormal tissue while removing a minimal quantity of healthy tissue. This invention is well suited to distinguishing between tissue types and therefore satisfying this need.

The medical profession often needs to have an objective assessment of the health of the tissue on a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient.

It is well known, for example, that early detection of tissues displaying pre-cancer or cancer modifications is important for successful medical treatment. We have already disclosed an apparatus and method for carrying out this detection. The invention described in this application represents a significant improvement on the apparatus disclosed in patent application Ser. No. 08/332,830, assigned to the same assignee as the current invention.

This new form of probe allows the doctor to perform an examination without the need to view the area under examination. Tactile feedback is employed to locate the area of interest after which the tip of the probe is passed over the area to be diagnosed.

The invention employs hybrid electronic technology to reduce the size of the diagnostic device enabling it to be mounted on the finger tip of a surgical glove. The necessary electrical connections are led down the finger and the glove to a remotely positioned control unit. The control unit provides power to the diagnostic device and analyzes the signals received from the device. Hybrid probe technology is described in our copending application filed this same date entitled "Hybrid Probe For Tissue Type Recognition".

To take advantage of the operator's ability to feel the area to be examined the diagnostic capsule is small compared with the area of the operator's finger tip. In this invention this is achieved by employing hybrid technology enabling an exceptionally high density of components. The attachments to the control unit are similarly kept small and lightweight to avoid distorting the feel of the tissue under examination. The connections are provided by means of thin wires having sufficient flexibility to enable the operator to trace the area under examination without restrictions. These wires and fibers are molded into the gloves to conform to the operator's hand.

An important application for this invention is in cervix examination. It is known that the use of a speculum during traditional examinations of the cervix is a major source of discomfort for patients leading to avoidance of the procedure. This invention avoids such discomfort so that many more women are willing to have the procedure performed at regular intervals.

An object of the present invention is to enable both electrical and optical measurements to be performed on the same area of tissue in a probe located at the tips of the fingers of a glove.

BRIEF DESCRIPTION OF THE DRAWINGS

FIG. 1 is a sectional view showing a preferred embodiment of the invention.

DETAILED DESCRIPTION OF A PREFERRED EMBODIMENT

Hybrid probe technology is generally described in our previously mentioned application "Hybrid Probe For Tissue Type Recognition". That application, which is incorporated herein by reference, generally disclosed an apparatus for identifying different tissue types including those displaying modifications involving precancerous or cancerous activity, said apparatus comprising a probe having one end shaped to face said tissue and having at least one radiation source towards the end of the probe and a detector for that radiation and a comparator to compare the measured received radiation with known values to thereby identify the tissue type. The apparatus also included electrodes to apply electrical signals to the tissue and electrical means to measure the resulting electrical response by said tissue.

One problem with such a configuration is the need to isolate light emitting and light receiving elements from one another. The hybrid probe was designed to examine areas of tissue having a diameter of the order of 2 mm, which requires that photodiode detectors be placed in close juxtaposition with light emitters yet optically isolated so that light signals do not pass directly from an emitter to a detector without intervention (i.e. backscattering) by the tissue under examination. This is accomplished in the present invention by the use of metal barriers. The metal barriers also shield the detector circuitry from electrical interference carried by current pulses that must be applied to the LEDs to induce them to emit light. The metal barrier may be left floating or grounded, but can also serve an additional role as an electrode for making electrical measurements to replace or supplement the two or three noble metal electrodes adjacent to the hybrid circuit normally used for the electrical measurements to be made on the tissue.

In addition the hybrid structure provides a preamplifier in close proximity to the photodiodes to amplify the small current from the photodiode detectors and feed it to the electronics in the handle of the probe and from there to the analysis circuitry.

A feature of the hybrid probe was that it eliminated the need for optical fibers to convey light signals, which if employed introduce temperature instabilities into the system, particularly at points where the optical fiber is bent.

FIG. 1 depicts the invention in a cross section. The finger 1 of the surgical rubber glove is fitted to the operator's finger 2. The hybrid optoelectronic circuit 3 is encased in the tip of the glove finger 1. Wires 4 from the circuit pass down the glove finger and back across the hand of the operator on their way to a controller.

Figure 2:
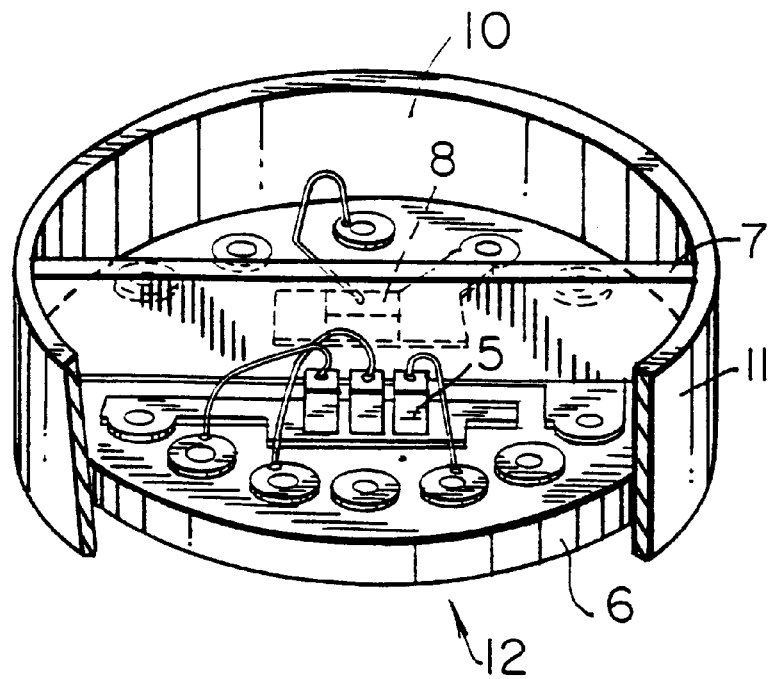
FIG. 2 is an illustration of the hybrid circuit intended for optical measurements.

FIG. 2 shows a preferred form of the hybrid circuit used to make optical measurements at three wavelengths of light. It is a perspective view of the circuit showing the placement of the optoelectronic components. The radiation sources 5 in this embodiment are LEDs, three of which are shown mounted on a substrate 6 together with other components. To control the direction of the radiation and to act as an electrostatic shield a barrier 7 divides the assembly into two chambers. This barrier is electrically conductive to provide electrical shielding. It can be grounded or left floating or serve as an electrode to receive and transmit electrical information. The radiation detector 8 is located in a second chamber.

Figure 3:
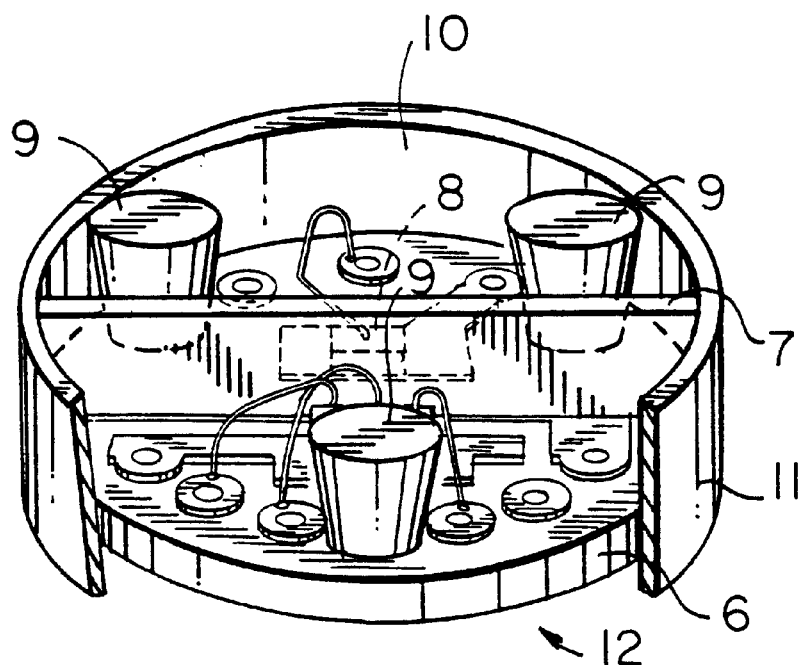
FIG. 3 is an illustration of the hybrid circuit including electrodes.

FIG. 3 illustrates a further preferred embodiment of the invention that includes electrodes 9 to enable electrical measurements to be made. Three electrodes are shown but the number can vary depending on other factors. The electrodes illustrated are circular but they may have other shapes. For example, kidney-shaped electrodes offer advantages since they can be of greater area than circular electrodes fitted into the same space. Kidney shapes are preferred to achieve greater electrode area without compromising optical performance or electrical resolution. Larger electrodes by their nature produce less noisy data because they sample a larger area of tissue whose average properties are less variable than a smaller area.

The space 10 is preferably filled with a transparent resin to retain the components in position and to protect them from damage. The assembly is mounted in a holder 11 which is mounted in the tip of the glove finger 1. An amplifier 12 mounted below the substrate 6 boosts the signal from the detector 8 which is conveyed back to the controller. The amplifier is mounted on a circuit board on the under side of the substrate 6.

A critical feature of this arrangement arises from the need to take special care with the shielding of the wiring from the detector 8 to its amplifier 12. The currents flowing in this wire may be of the order of nanoamperes. The drive current to the nearby LEDs may be as high as 100 milliamperes. Shielding is vital since the ratio of these currents is huge. In addition the patient's body and the operators finger may generate substantial voltage signals caused by adjacent wiring or other electrical equipment operated nearby. The detector circuit is shielded from this source of interference as well. This is achieved by the preferred use of multilayer circuit boards in the substrate 6 to convey the signals. The disposition of the signals flowing in the tracks on these boards is chosen to avoid unwanted capacitive or electromagnetic coupling.

The optical layout needs to be carefully planned because of the conflicting demands made on it. To achieve an adequate level of illumination the LEDs 5 are placed as close as possible to the tissue although as the efficiency of LEDs continues to improve the above considerations may become less critical. There are two limits to how small the distance can be made from the top of the LEDs to the tissue. The first limit is the need to accommodate the bond wires from the top of the LEDs, which tend to loop upward from the surface of the die. The second limit arises from optical considerations. It is important to control the direction and angle of the illumination of the tissue surface so that detector circuits behave consistently. If the distance between the optoelectronics and the tissue varies, the sensitivity of the devices will vary. Tissue recognition will thereby be impaired. The distance from the LEDs to the tissue surface should therefore be kept large enough so that assembly tolerances do not lead to uncontrolled variability between probes. Since the position and size of the LED top surface can typically be controlled to within plus or minus 25 micrometers, this uncertainty should preferably not be more than approximately 5% of the LED to surface distance. That distance should therefore be not less than 0.5 millimeter.

The lateral placement of the die comprising the LEDs is similarly controlled to only 25 micrometers so this needs to be part of the geometric considerations. A more deeply placed die will be less sensitive to errors in placement.

The lateral placement also affects the diagnostic ability of the device by modifying the depth of penetration of the radiation prior to its return to the detector. It is important therefore that the placement be chosen to achieve the desired depth of penetration bearing in mind the tolerances on the accuracy that can be maintained. In general the closer the optoelectronics components 5 and 8 are to the barrier 7, the smaller the depth of penetration.

It can be seen from the above descriptions that the preferred embodiments of the invention are small enough that when fitted to the tip of a glove they do not interfere with the ability of the operator to feel his or her way around the organs to be diagnosed.

Although the invention has been described in terms of preferred embodiments it is intended that the protection afforded by this patent cover the substitution of equivalents for any of the elements of the following claims.

What is claimed is:

1. An apparatus for identifying physiologically different tissue types, said apparatus comprising:
    a close packed array in the tip of a finger portion of a glove comprising
        a light emitting die configured to irradiate a tissue;
        a detector die configured to receive radiation backscattered by said tissue when the tip of finder portion of the glove contacts said tissue;
        a shield between said light emitting die and said detector die, said shield preventing leakage of optical and electrical signals from said light emitting die to said detector die;
        emitter and detector circuits respectively associated with said emitting die and said detector die,
        a controller coupled to said emitting die and said detector die, said controller adapted to drive said emitter and detector circuits and to analyze signals produced by said circuits.

2. The apparatus for identifying physiologically different tissue types of claim 1, said apparatus further comprising an electrode configured to supply electrical signals to said tissue and to measure the response of the tissue.

3. The apparatus for identifying physiologically different tissue types of claim 1, wherein wiring is led from said detector circuit in the tip of the glove via a finger of the glove and the hand of the glove to said controller.

4. The apparatus for identifying physiologically different tissue types of claim 2, wherein wiring is led from said detector circuit in the tip of the glove via a finger of the glove and the hand of the glove to said controller.

5. The apparatus for identifying physiologically different tissue types of claim 2, wherein said electrode is shaped to achieve a large area of electrode.

6. The apparatus for identifying physiologically different tissue types of claim 5, wherein said electrode is kidney shaped.

7. A method for identifying physiologically different tissue types comprising inserting against a tissue surface a close packed array in the tip of a finger portion of a glove comprising a light emitting die configured to irradiate a tissue, said light emitting die comprises LEDs;

a detector die configured to receive radiation backscattered by said tissue;

a shield between said light emitting die and said detector die, said shield preventing leakage of optical and if electrical signals from said light emitting die to said detector die;

emitter and detector circuits respectively associated with said emitting die and said detector die, a controller coupled to said emitting die and said detector die, said controller adapted to drive said emitter and detector circuits and to analyze signals produced by said circuits, applying a current to the LEDs and measuring the voltage drop to determine the temperature of the LEDs, calculating a correction for the radiation output from the LEDs in order to apply an adjustment to the measured values of signals from the detector die.

\* \* \* \* \*